United States Patent [19]
Friedhoff et al.

[11] Patent Number: 4,925,873
[45] Date of Patent: May 15, 1990

[54] METHOD OF TREATING SKIN INJURIES USING THROMBOXANE A₂ RECEPTOR ANTAGONISTS

[75] Inventors: Lawrence T. Friedhoff, New York, N.Y.; Laura L. Bolton, Metuchen, N.J.

[73] Assignee: E. R. Squibb & Sons, Inc., Princeton, N.J.

[21] Appl. No.: 239,376

[22] Filed: Sep. 1, 1988

[51] Int. Cl.⁵ .................. A61K 31/34; A61K 31/19; A61K 31/195
[52] U.S. Cl. ................................... 514/469; 514/562; 514/568; 514/570; 514/571
[58] Field of Search ............... 514/469, 562, 568, 570, 514/571

[56] References Cited

U.S. PATENT DOCUMENTS

| | | | |
|---|---|---|---|
| 4,416,896 | 11/1983 | Nakane et al. | 514/469 |
| 4,663,336 | 5/1987 | Nakane et al. | 514/381 |
| 4,673,685 | 6/1987 | Varma et al. | 514/333 |

OTHER PUBLICATIONS

R. Rees et al., Mechanism of Platelet Injury Associated with Dermonecrosis Resulting from Brown Recluse Spider Vernom., *Clinical Research*, 30:265A, 1982.

E. J. Del Beccar et al., The Use of Specific Thromboxane Inhibitors to Preserve the Derman Microcirculation After Burning, *Surgery*, 87(2):137–141, 1980.

S. Lelcuk et al., Prostacyclin (PG12) and Thromboxane (Tx)A2: Mediators of Wound Healing, *Isr. J. Med. Sci.*, (23, No. 7, 841–43, 1987).

J. P. Heggers et al., Histological Demonstration of Prostaglandins and Thromboxanes in Burned Tissue, *Journal of Surgical Research*, 28(2):110–117, 1980.

M. C. Robson et al., A New Explanation for the Progressive Tissue Loss in Electrical Injuries, *Plastic and Reconstructive Surgery*, 73(3):431–437, 1984.

M. C. Robson et al., The Effect of Prostaglandins on the Dermal Microcirculation After Burning, and the Inhibition of the Effect by Specific Pharmacological Agents, *Plastic and Reconstructive Surgery*, 63(6):781–787, 1979.

L. S. Zachary et al., Combined Prostacyclin and Thromboxane Synthetase Inhibitor UK 38485 in Flap Survival, *Annals of Plastic Surgery*, 17(2):112–115, 1986.

J. Backon, Use of a Novel Thromboxane Synthetase Inhibitor in Burns, *Burns Incl. Therm. Inj. (England)*, Jun., 1987, 13(3), p. 252.

J. P. Heggers et al., Thromboxane Inhibitors for the Prevention of Progressive Dermal Ischemia due to the Thermal Injury, *J Burn Care Rehabil.*, Nov.–Dec., 1985, 6(6), pp. 466–468.

S. L. Wang et al., The Effect of the Thromboxane Synthetase Inhibitor Dazmegrel (UK-38,485) on Wound Healing, Dermal Ink Perfusion and Skin Blood Flow Measurements in Deep Partial Thickness Burns, *Burns Incl. Therm. Inj.*, Jun. 1986, 12(5), pp. 312–317.

M. C. Robson et al., Increasing Dermal Perfusion After Burning by Decreasing Thromboxane Production, *J Trauma*, Sep. 1980, 20(9), pp. 722–725.

J. R. Saranto et al., Blisters, Cooling, Antithromboxanes, and Healing in Experimental Zone-of-Stasis Burns, *J Trauma*, Oct. 1983, 23(10), pp. 927–933.

F. Alexander et al., Arachidonic Acid Metabolites Mediate Early Burn Edema, *J Trauma*, Aug. 1984, 24(8), pp. 709–712.

R. L. McCauley et al., Frostbite Injuries: A Rational Approach Based on the Pathophysiology, *J Trauma*, Feb. 1983, 23(2), pp. 143–147.

*Primary Examiner*—Leonard Schenkman
*Attorney, Agent, or Firm*—Burton Rodney

[57] ABSTRACT

A method for treating skin injuries is provided by administering a thromboxane-A₂ receptor antagonist systemically or topically to the skin area to be treated.

14 Claims, No Drawings

METHOD OF TREATING SKIN INJURIES USING THROMBOXANE A₂ RECEPTOR ANTAGONISTS

FIELD OF THE INVENTION

The present invention relates to a method of treating skin injuries in mammalian species by administering a thromboxane A$_2$ receptor antagonist to facilitate healing and/or limit extent of such skin injuries.

BACKGROUND OF THE INVENTION

It is known that thromboxane A$_2$ plays a role in ischemic tissue damage. A number of human studies have demonstrated that aspirin, an inhibitor of thromboxane production, decreases the incidence of stroke (cerebral ischemia) and myocardial infarction (myocardial ischemia) in certain patient populations. The role of thromboxane in skin injury is less clear. However, evidence from animal studies suggests that thromboxane A$_2$ plays an important role in skin injury.

Thromboxane A$_2$ is present in burned skin (J. P. Heggers, G. L. Loy, M. C. Robson, and E. J. Del Beccaro, Histological Demonstration of Prostaglandins and Thromboxanes in Burned Tissue, *Journal of Surgical Research*, 28(2):110–117, 1980) and systemically administered imidazole, methyl prednisolone and topical Dermoid Aloe, nonspecific inhibitors of thromboxane production diminish injury following electrical burns (M. C. Robson, R. C. Murphy, and J. P. Heggers. A New Explanation for the Progressive Tissue Loss in Electrical Injuries, *Plastic and Reconstructive Surgery*, 73(3):431–437, 1984 and J. P. Heggers, M. C. Robson, and L. S. Zachary, Thromboxane Inhibitors for the Prevention of Progressive Dermal Ischemia Due to the Thermal Injury, *Burn Care*, 6(6):466–468, 1985). Adrenal steroids, indomethacin, aspirin, and methimazole (all nonspecific inhibitors of thromboxane A$_2$ synthesis) preserve skin blood flow and improve healing following scald burns (M. C. Robson, E. J. Del Beccaro, and J. P. Heggers, The Effect of Prostaglandins on the Dermal Microcirculation After Burning, and the Inhibition of the Effect by Specific Pharmacological Agents *Plastic and Reconstructive Surgery*, 63(6):781–787, 1979 and E. J. Del Beccaro, M. C. Robson, J. P. Heggers, and R. Swaminathan, The Use of Specific Thromboxane Inhibitors to Preserve the Dermal Microcirculation After Burning, *Surgery*, 87(2):137–141, 1980). Furthermore, topical administration of imidazole, or UK 38485 or U 63557A (nonspecific inhibitors of thromboxane A$_2$ synthesis) improved healing following scald burns (J. P. Heggers et al, *Burn Care*, 6(6):466–468, 1985). In a model of traumatic skin injury, UK 38485 increased tissue survival (L. S. Zachary, J. P. Heggers, M. C. Robson, R. C. Murphy, Combined Prostacyclin and Thromboxane Synthetase Inhibitor UK 38485 in Flap Survival. *Annals of Plastic Surgery*, 17(2):112–115, 1986).

In addition, the results of in vitro studies suggest that the platelet release reaction (a thromboxane A$_2$ dependent process) plays a role in the platelet injury associated with dermonecrosis following the bite of the venomous brown recluse spider (R. Rees, J. Hawiger, R. M. Des Prez, and L. E. King, Mechanism of Platelet Injury Associated with Dermonecrosis Resulting from Brown Recluse Spider Venom, *Clinical Research* 30:265A, 1982).

To date, studies of the role of thromboxane A$_2$ in skin injury have used inhibitors that are nonspecific, altering the production of multiple substances in addition to thromboxane A$_2$.

DESCRIPTION OF THE INVENTION

In accordance with the present invention, a method is provided for treating skin injuries caused by trauma or thermal burns wherein a thromboxane A$_2$ receptor antagonist is systemically or topically administered during or after exposure of skin to trauma or thermal burns, to facilitate healing and/or limit the extent of such injuries.

In addition, in accordance with the present invention, a method is provided for preventing or treating skin pressure injuries, for example, bed sores, wherein a thromboxane A$_2$ receptor antagonist is systemically administered or topically administered to the skin, prior to, during or after exposure of such skin to pressure injury.

Thromboxane A$_2$ antagonists which may be employed herein are specific inhibitors of the actions of thromboxane A$_2$ and therefore produce the desired effect of thromboxane A$_2$ inhibition without causing other non-specific effects that may be undesirable. Examples of such thromboxane A$_2$ antagonists suitable for use herein include but are not limited to the 7-oxabicycloheptane and 7-oxabicycloheptene compounds disclosed in U.S. Pat, No. 4,537,981 to Snitman et al, especially, [1S-[1α,2β(5Z),3β(1E,3R,4S),4α]]-7-[3-(3-hydroxy-4-phenyl-1-pentenyl)-7-oxabicyclo-[2.2.1]hept-2-yl]-5-heptenoic acid; the 7-oxabicycloheptane substituted amino-prostaglandin analogs disclosed in U.S. Pat. No. 4,416,896 to Nakane et al., especially, [1S-[1α,2β(5Z),3β,4α]]-7-[3-[[2-(phenylamino)carbonyl]hydrazino]methyl]-7-oxabicyclo[2.2.1]hept-2-yl]-5-heptenoic acid; the 7-oxabicycloheptane substituted diamide prostaglandin analogs disclosed in U.S. Pat. No. 4,663,336 to Nakane et al, especially, [1S-[1β,2α(5Z),3α,4β]]-7-[3-[[[[(1-oxoheptyl)amino]acetyl]amino]methyl]-7-oxabicyclo[2.2.1]-hept-2-yl]-5-heptenoic acid (SQ 30,471), which is preferred, and the corresponding tetrazole, and [1S-[1α,2β(Z),3β,4α]]-7-[3-[[[[(4-cyclohexyl-1-oxobutyl)amino]acetyl]amino]-methyl]-7-oxabicyclo[2.2.1]hept-2-yl]-5-heptenoic acid; the phenoxyalkyl carboxylic acids disclosed in U.S. Pat. No. 4,258,058 to Witte et al, especially 4-[2-(benzenesulfamido)ethyl]phenoxyacetic acid, (BM 13,177 —Boehringer Mannheim), the sulphonamidophenyl carboxylic acids disclosed in U.S. Pat. No. 4,443,477 to Witte et al, especially 4-[2-(4-chlorobenzenesulfonamido)ethyl]-phenylacetic acid, (BM 13,505, Boehringer Mannheim) the arylthioalkylphenyl carboxylic acids disclosed in U.S. Pat. No. 4,752,676 especially 4-(3-((4-chlorophenyl)sulfonyl)propyl)benzeneacetic acid.

Other examples of thromboxane A$_2$ inhibitors suitable for use herein include, but are not limited to (E)-5-[[[(pyridinyl)[3-(trifluoromethyl)phenyl]methylene]amino]oxy]pentanoic acid also referred to as R68,070 - Janssen Research Laboratories, 3-[1-(4-chlorophenylmethyl)-5-fluoro-3-methylindol-2-yl]-2,2-dimethylpropanoic acid [(L-655240 Merck-Frosst) Eur. J. Pharmacol. 135(2):193, 17 Mar. 87], 5(Z)-7-([2,4,5-cis]-4-(2-hydroxyphenyl)-2-trifluoromethyl-1,3-dioxan-5-yl)heptenoic acid (ICI 185282, Brit. J. Pharmacol 90 (Proc. Suppl):228 P-Abs., Mar. 87), 5(Z)-7-[2,2-dimethyl-4-phenyl-1,3-dioxan-cis-5-yl]heptenoic acid (ICI 159995, Brit. J. Pharmacol. 86 (Proc. Suppl):808 P-Abs., Dec. 85), N,N'-bis[7-(3-chlorobenzeneaminosulfonyl)-1,2,3,4-tetrahydro-isoquinolyl]disulfonylimide (SKF 88046, Pharmacologist 25(3):116 Abs, 117 Abs, Aug.

83), [1α(Z)-2β,5α]-(+)-7-[5-[[(1,1'-biphenyl)-4-yl]methoxy]-2-(4-morpholinyl)-3-oxocyclopentyl]-4-heptenoic acid (AH 23848 - Glaxo, Circulation 72(6):1208, Dec. 85, levallorphan allyl bromide (CM 32,191, Sanofi, Life Sci. 31 (20-21):2261, 15 Nov. 82), (Z,2-endo-3-oxo)-7-(3-acetyl-2-bicyclo[2.2.1]heptyl-5-hepta-3Z-enoic acid, 4-phenylthiosemicarbazone (EP092 —Univ. Edinburgh, Brit, J. Pharmacol. 84(3):595, Mar. 85).

The disclosure of the above-mentioned patents, patent applications and other references are incorporated herein by reference.

In carrying out the method of the present invention, the thromboxane $A_2$ receptor antagonist may be administered to mammalian species, such as monkeys, dogs, cats, rats, humans.

Although the thromboxane $A_2$ receptor antagonist may be administered systemically, such as orally or parenterally, it is preferred that the thromboxane $A_2$ receptor antagonist be administered locally so that it may be absorbed in the injured skin area. Where a pressure injury such as bed sores may be a problem, the thromboxane $A_2$ receptor antagonist may be used prophylactically as well.

The topical compositions which may be employed herein will include a topical carrier which may take the form of a cream, lotion, ointment, gel, lipophilic stick, liquid, powder, aerosol and the like. Examples of such topical carriers are set out in U.S. Pat. Nos. 3,892,856, 3,892,857, 4,082,881 and 4,233,295, the disclosures of which are incorporated herein by reference.

With regard to dosage of thromboxane $A_2$ receptor antagonist, where the drug is administered topically, the topical formulation will contain from about 0.01 to 5% by weight thromboxane $A_2$ receptor antagonist. The number of applications will depend upon the extent of the skin injury. Usually, from 1 to 5 treatments per day for 5 days will be required. Although, when used prophylactically, the topical formulation may be applied for as long as possibility of skin injury continues.

The thromboxane $A_2$ antagonist may also be incorporated in a conventional dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid or sodium bisulfite) or the like. Oral dosage forms are preferred, although parenteral forms are quite satisfactory as well.

With regard to such systemic formulations, single or divided doses of from about 5 to about 2500 mg, preferably from about 10 to 2000 mg/one to four times daily, may be administered in systemic dosage forms as described above for a period sufficient to facilitate healing and decrease skin injury.

The following Examples represent preferred embodiments of the present invention.

EXAMPLE 1

A thromboxane receptor $A_2$ antagonist formulation suitable for oral administration is set out below.

1000 tablets each containing 400 mg of thromboxane $A_2$ antagonist were produced from the following ingredients.

[1S-[1β,2α(5Z),3α,4β]]-7-[3-[[[[(1-Oxoheptyl)amino]acetyl]amino]methyl]-7-oxabicyclo[2.2.1]hept-2-yl]-5-heptenoic acid (SQ 30,741) 400 g
Corn starch 50 g
Gelatin 7.5 g
Avicel (microcrystalline cellulose) 25 g
Magnesium stearate 2.5 g The thromboxane antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredient.

EXAMPLES 2 AND 3

The following topical aerosol formulations may be used in treating skin injury.

| Example 2 | | Amount % by Wt. | Specific Amount % by Wt. |
|---|---|---|---|
| SQ 30,471 | | 0.01 to 1 | 0.05 |
| Ethanol | | 5–50 | 25 |
| Freon 11 or 114 | 50–50 | | |
| Freon 12 | mixture | 50–95 | 74.95 |

| Example 3 | | % by Wt. |
|---|---|---|
| SQ 30,741 | | 0.01–1 |
| Surfactant (Oleic acid, oleyl alcohol, lecithin) | | qs. |
| Water | | qs. |
| Freon 11 or 114 | 50–50 | |
| Freon 12 | mixture | qs. to 100% |

EXAMPLE 4

An injectable solution for use in administering thromboxane $A_2$ receptor antagonist is produced as follows:
[1S-[1α,2β(5Z),3β,4α]]-7-[3-[[2-(phenylamino)carbonyl]hydrazino]methyl]-7-oxabicyclo[2.2.1]hept-2-yl]-5-heptenoic acid (SQ 29,548) 2500 mg
Methyl paraben 5 mg
Propyl paraben 1 mg
Sodium chloride 25 g
Water for injection qs. 5 l.

The thromboxane $A_2$ antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

EXAMPLE 5

An injectable for use in treating skin injury is prepared as described in Example 4 except that the thromboxane $A_2$ antagonist employed is the phenoxyalkyl carboxylic acid 4-2-(benzenesulfamido)ethyl]phenoxyacetic acid, disclosed in U.S. Pat. No. 4,258,058.

EXAMPLE 6

An injectable for use in treating skin injury is prepared as described in Example 4 except that the thromboxane $A_2$ antagonist employed is [1S-[1α,2β(Z),3β,4']]-7-[3-[[[[(4-cyclohexyl-1-oxobutyl)amino]acetyl]amino]methyl]-7-oxabicyclo[2.2.1]hept-2-yl]-5-heptenoic acid.

EXAMPLE 7

An oral, injectable or topical solution for use in treating skin injury is prepared as follows.

SQ 30,741 solution at 50 mg/ml concentration is prepared by suspending an appropriate amount of SQ 30,741 in distilled water and adjusting the pH to 12.0 with 1N NaOH to obtain a clear solution. The solution is then back-titrated to pH 8.0 with dilute phosphoric acid, the volume adjusted with distilled water and the solution is filtered through a 0.45 μm filter. Solutions in the concentration range of 0.1–10.0 mg/ml are prepared by serial dilution of the filtered 50 mg/ml solution.

EXAMPLE 8

An oral, injectable or topical suspension for use in treating skin injury is prepared as follows.

SQ 30,741 suspensions are prepared in 1% carboxymethylcellulose (CMC) solution. One percent CMC solution is prepared in distilled water and titrated to pH 8.2 with sodium bicarbonate. The 1% CMC solution is added slowly to the appropriate amount of SQ 30,741 powder in volumetric flask to obtain uniform dispersion. Volume is made up with 1% CMC.

The following additional topical formulations are prepared as described below.

EXAMPLE 9

Cream Containing 0.5% SQ 30,741

SQ 30,741, micronized 0.5 gm
Dibutyl sebacate 5 gm
Glyceryl stearate 4 gm
White wax 4 gm
Promulgen, Type D (PEG fatty alcohol ether)-Cetearyl alcohol and Ceteareth-20 (Robinson-Wagner) 7 gm
Propylene glycol 15 gm
Dimethicone 350 1 gm
Purified water, sufficient to make 100.0 gm The SQ 30,741 is mixed with dibutyl sebacate with gentle heat not over 50° C. The glyceryl stearate, white wax, Dimethicone 350 and Promulgen are melted together and heated to 75°–80° C., cooled to room temperature and then mixed with the above solution and the propylene glycol. The resulting mixture is added to purified water with vigorous agitation to emulsify and agitate. Sufficient purified water is then added to make 100 gm. Mixing is then continued at a slow rate during the congealing stage until the cream reaches room temperature.

EXAMPLE 10

Lotion 0.7%

SQ 30,741 0.7 gm
Dibutyl sebacate 7 gm
Polysorbate 60 5 gm
Sodium carboxymethyl cellulose 5 gm
Cetyl alcohol 2 gm
Methylparaben 0.3 gm
Propylparaben 0.03 gm
Purified water q.s. 100 gm The SQ 30,741 and parabens are mixed with dibutyl sebacate with gentle heat, not over 50° C., and melted together and Polysorbate 60 and cetyl alcohol added. Water is heated to 80° C. to dissolve the sodium carboxymethyl cellulose forming an aqueous phase which is added with vigorous agitation to the oil phase to emulsify. Agitation is continued until the temperature drops down to 48° C. Sufficient 50° C. water is added to make 100 gm. Mixing is continued at a slow rate to congeal the mixture, until the lotion drops down to room temperature.

EXAMPLE 11

Ointment, 0.5%

SQ 30,741 0.5 gm
(a) Dibutyl sebacate 50 gm
(b) Mineral Oil 44 gm
(a) and (b) gelled with polyethylene 5 gm
Titanium dioxide 0.5 gm The SQ 30,741 is mixed with dibutyl sebacate, and added to a gelled mixture of mineral oil and polyethylene containing titanium dioxide.

EXAMPLE 12

Lotion 0.5%

SQ 29,548 0.5 gm
Dimethylisosorbide U.S.P. 45 gm
Petrolatum, U.S.P. 3 gm
Promulgen, Type D (PEG fatty alcohol ether)-Cetearyl alcohol and Ceteareth-20 (Robinson-Wagner) 1.5 gm
Methylparaben, U.S.P. 0.15 gm
Propylparaben 0.02 gm
Purified water, sufficient to make 100 gm The SQ 29,548 and parabens are mixed with dimethylisosorbide with gentle heat not over 50° C. The petrolatum and Promulgen are melted together and heated to 75°–80° C., cooled to room temperature and then mixed with the above solution. The resulting mixture is added to purified water with vigorous agitation to emulsify. Agitation is continued until the temperature drops down to 48° C. Sufficient hot (48°–50° C.) purified water is then added to make 100 gm. Mixing is then continued at a slow rate during the congealing stage until the temperature of the lotion reaches 42° C.

EXAMPLE 13

Topical Cream, 0.1%

SQ 30,741 0.1 gm
Dimethylisosorbide 55 gm
Petrolatum, U.S.P. 16 gm
Promulgen, Type D (PEG fatty alcohol ether) 8 gm
Methylparaben 0.15 gm
Propylparaben 0.02 gm
Purified water, sufficient to make 100 gm The SQ 30,741 and parabens are mixed with dimethylisosorbide with gentle head, not over 50° C. Petrolatum and Promulgen D are melted together. After mixing, the mixture is added to the dimethylisosorbide solution with thorough mixing, maintaining the temperature at below 50° C. Water is added with vigorous agitation to the oil phase to emulsify. Agitation is continued until the temperature drops down to 48° C. Sufficient 50° C. water is added to make 100 gm. Mixing is continued at a slow rate to congeal the mixture until the temperature drops down to 42° C.

EXAMPLE 14

Ointment, 0.25%

SQ 29,548 0.25 gm
Dimethylisosorbide 1 gm
Titanium dioxide 0.5 gm
Plastibase 50W (mineral oil) (95%) gelled with polyethylene (5) sufficient to make 100 gm The SQ 29,548 is mixed with dimethylisosorbide with gentle heat not over 50° C. The solution is cooled to room temperature and titanium dioxide is dispersed homogeneously into the oil. The suspension is incorporated into the Plastibase by slow rate of mixing until homogeneous to form the ointment.

EXAMPLE 15

Lipophilic Clear Gel, 0.5%

SQ 30,741 0.5 gm
Dimethylisosorbide 1 gm
Mineral oil, U.S.P. 80.375 gm
Paraflint RG (High melting paraffin wax), Moore and Munger 6 gm
Span 65 (Sorbitan tristearate, ICI) 3.6 gm Paraflint RG and Span 65 are melted and heated to 100° C. The molten mixture is incorporated in hot (100° C.) mineral oil and mixed well. The temperature of the oil is quickly brought to 50° C. to form a gel.

The SQ 30,741 is mixed with dimethylisosorbide by gentle heat, the oil is cooled to room temperature and then is incorporated in the gel homogeneously.

EXAMPLE 16

Lipophilic Stick

SQ 30,741 % 0.1 gm
Dimethylisosorbide 2.5 gm
Carnauba wax 8 gm
Beeswax 16 gm
Petrolatum 3.4 gm
Ceraphyl 365, Van Dyk (Isostearyl Neo Pentanoate) 10 gm The SQ 30,741 is mixed with dimethylisosorbide with gentle heat not over 50° C. A molten mixture of the remaining ingredients is added to the above solution at 50° C. The mixture is poured into a mold and chilled to solidify the mixture to a stick.

EXAMPLES 17–21

Topical creams are formulated from the following ingredients:
A. SQ 30,741
B. Glyceryl monostearate
C. Cetyl alcohol
D. Myristyl stearate
E. Isopropyl palmitate
F. Tween 60
G. Propylene glycol
H. Water U.S.P.

| Ingredient | Example 17 | 18 | 19 | 20 | 21 |
|---|---|---|---|---|---|
| | Parts by Weight | | | | |
| A. | 0.05 | 0.1 | 1 | 1 | 2 |
| B. | 120 | 94 | 94 | 70 | 94 |
| C. | 29 | 22 | 22 | 18 | 22 |
| D. | 65 | 56 | 56 | 44 | 56 |
| E. | 27 | 22 | 22 | 18 | 22 |
| F. | 33 | 33 | 33 | 33 | 33 |
| G. | 300 | 400 | 600 | 700 | 700 |
| H. | 438 | 373 | 171 | 116 | 70 |
| % by weight of SQ 30,741 in solution | 35 | 59 | 39 | 71 | 58 |

Procedure (1) The myristyl stearate, cetyl alcohol, glyceryl monostearate, isopropyl palmitate and about one-third of the Tween 60 are heated to about 90° and melted. (2) SQ 30,741 is mixed with about of the propylene glycol with gentle warming. (3) The balance of the Tween 60 is mixed with the water, the mixture heated to about 50° and added to the SQ 30,741-propylene glycol mixture which is also at a temperature of about 90°. (4) The oil phase from step 1 is added to the aqueous glycol phase and mixed rapidly at about 90°. The mixing is continued until emulsification is complete. The cream is then cooled to room temperature. (5) The remaining SQ 30,741 is slurried in the remaining propylene glycol and blended into the cream at room temperature until uniform.

EXAMPLE 22

Ointment

| Ingredients | Example 22 Ointment Parts by Weight |
|---|---|
| Polyethylene glycol* 1500 | 10.0 |
| Polyethylene glycol 400 | 10.0 |
| Polyethylene glycol 6000 distearate | 2.0 |
| SQ 30,741 | 0.1 |
| White petrolatum, U.S.P. | 77.9 |
| Total | 100.0 |

*An equal part mixture of polyethylene glycol 300 and 1540

Procedure

The polyethylene glycols and polyethylene glycol 6000 distearate are combined and heated with stirring to 65° C. In a suitable stainless steel or glass lined kettle jacketed and equipped for heating and cooling. The SQ 30,741 is then added to the molten mixture and the heating and stirring continued for approximately 20 minutes. At this time, the petrolatum which has been separately melted is added. After addition is complete, stirring is resumed. Heating is discontinued and the composition allowed to cool with stirring until congealing begins (approximately 46° C.). The resulting ointment has the petrolatum as the continuous phase and the polyethylene glycol having the SQ 30,741 dissolved therein as the discontinuous phase.

Satisfactory preparations may also be prepared by reversing the above operation, i.e., adding the glycol phase to the melted petrolatum phase.

What is claimed is:

1. A method of treating skin injury in mammalian species caused by trauma or thermal burns, or skin pressure injuries, which comprises administering to a mammalian species in need of such treatment an effective amount of a thromboxane $A_2$ receptor antagonist.

2. The method as defined in claim 1 wherein the thromboxane $A_2$ receptor antagonist is administered intravenously, orally or topically.

3. The method as defined in claim 1 wherein the thromboxane $A_2$ receptor antagonist is administered prior to, during or after a skin pressure injury.

4. The method as defined in claim 1 wherein the thromboxane $A_2$ receptor antagonist is administered during or after a skin injury.

5. The method as defined in claim 1 wherein the thromboxane $A_2$ antagonist is administered topically.

6. The method as defined in claim 1 wherein in thromboxane $A_2$ antagonist is a 7-oxabicycloheptane substituted amino-prostaglandin analog.

7. The method as defined in claim 1 wherein the thromboxane $A_2$ antagonist is a 7-oxabicycloheptane substituted diamide prostaglandin analog, a phenoxyalkyl carboxylic acid, a sulfonamidophenyl carboxylic acid, or an arylthioalkylphenyl carboxylic acid.

8. The method as defined in claim 1 wherein the thromboxane $A_2$ antagonist is [1S-[1α,2β(5Z),3β(-1E,3R,4S),4α]]-7-[3-(3-hydroxy-4-phenyl-1-pentenyl)-7-oxabicyclo[2.2.1]hept-2-yl]-5-heptenoic acid.

9. The method as defined in claim 1 wherein the thromboxane $A_2$ antagonist has the name [1S-[1β,2α(5Z),3α,4β]]-7-[3-[[[(1-oxoheptyl)amino]acetyl]amino]methyl]-7-oxabicyclo[2.2.1]- hept-2-yl]-5-heptenoic acid or the corresponding tetrazole.

10. The method as defined in claim 1 wherein the thromboxane $A_2$ antagonist has the name [1S-[1α,2β(Z),3β,4α]]-7-[3-[[[[(4-cyclohexyl-1-oxobutyl)amino]acetyl]amino]methyl]-7-oxabicyclo[2.2.1]hept-2-yl]-5-heptenoic- acid.

11. The method as defined in claim 1 wherein the thromboxane $A_2$ antagonist has the name [1S-[1α,2β(5Z),3β,4α]]-7-[3-[[2-(phenylamino)carbonyl]hydrazino]methyl]-7-oxabicyclo2.2.1]hept-2-yl]-5-heptenoic acid.

12. The method as defined in claim 1 wherein the thromboxane $A_2$ antagonist has the name 4-(3-((4-chlorophenyl)sulfonyl)propyl)benzene acetic acid.

13. The method as defined in claim 1 wherein the thromboxane $A_2$ antagonist has the name or 4-[2-(benzenesulfamido)ethyl]phenoxyacetic acid or 4-[2-(4-chlorobenzenesulfonamido)ethyl-]phenylacetic acid.

14. The method as defined in claim 1 wherein the thromboxane $A_2$ receptor antagonist is a 7-oxabicycloheptane prostaglandin analog.

* * * * *